United States Patent [19]

Sakuma et al.

[11] Patent Number: 5,411,039
[45] Date of Patent: May 2, 1995

[54] APPARATUS FOR AUTOMATICALLY TAKING IN SMOKE OF ROLLED TOBACCOS AND ANALYZING THE SAME

[75] Inventors: Yuzuru Sakuma; Keisuke Minami; Hiroyoshi Suda, all of Hiratsuka, Japan

[73] Assignee: Japan Tobacco Inc., Tokyo, Japan

[21] Appl. No.: 99,577

[22] Filed: Jul. 30, 1993

[30] Foreign Application Priority Data

| Jul. 31, 1992 | [JP] | Japan | 4-205671 |
| Jul. 31, 1992 | [JP] | Japan | 4-205672 |
| Jul. 31, 1992 | [JP] | Japan | 4-205673 |
| Jul. 31, 1992 | [JP] | Japan | 4-205674 |
| Jul. 31, 1992 | [JP] | Japan | 4-205675 |

[51] Int. Cl.⁶ .................................................. A24C 5/32
[52] U.S. Cl. .................................................. 131/330
[58] Field of Search .................................................. 131/330

[56] References Cited

U.S. PATENT DOCUMENTS

3,548,841 12/1970 Caughey.
3,586,007 6/1971 Kelley et al. .................. 131/330
3,732,874 5/1973 Wagner et al. .................. 131/330
4,858,628 8/1989 Norman et al. .

FOREIGN PATENT DOCUMENTS

21083 1/1981 European Pat. Off. .
417974 3/1991 European Pat. Off. .
1757660 5/1971 Germany .

OTHER PUBLICATIONS

Elmhorst et al., Tobacco Abstracts, Oct. 1969, No. 2731.
Moshy et al., "*Smoking Machine*—Automatic, Versatile", *Tobacco,* Apr. 1968, pp. 22–24.

*Primary Examiner*—Jennifer Bahr

[57] ABSTRACT

An apparatus for automatically taking in smoke of rolled tobaccos and automatically analyzing the smoke includes a mounting and demounting unit for mounting a rolled tobacco in and demounting the same from each smoke inlet provided in a main body, an end position detecting unit for detecting the tip of each rolled tobacco, an extinguishing position detecting unit for detecting the extinguishing position of each rolled tobacco, a lighting unit for lighting the tip of each rolled tobacco, cutting-off unit for cutting off the burnt portion of each rolled tobacco at its extinguishing portion, and an operating unit for moving the lighting unit to the tip of each rolled tobacco held in the respective smoke inlet and detected by the tip position detecting unit so as to light the tip of the rolled tobacco and for causing the extinguishing position detecting unit to detect that the rolled tobacco is burning at its extinguishing position is burning, and for causing the cutting-off unit to cut off the burnt portion of the rolled tobacco.

10 Claims, 10 Drawing Sheets

APPARATUS FOR AUTOMATICALLY TAKING IN SMOKE OF ROLLED TOBACCOS AND ANALYZING THE SAME

BACKGROUND OF THE INVENTION

1. Field of the Invention

This invention relates to an apparatus for automatically taking in smoke of rolled tobaccos such as cigarettes or cigars and analyzing the same, and more particularly to an automatic smoke analyzing apparatus which can change, light and extinguish the rolled tobaccos automatically so as to eliminate all manual operation.

2. Description of the Related Art

Upon manufacturing and selling rolled tobaccos such as cigarettes or cigars, the contents of chemical substances in tobacco smoke such as nicotine and tar must be indicated.

Like other agricultural products, the chemical properties of tobacco leaves are not accurately uniform. It is necessary, therefore, to sample rolled tobaccos at a predetermined rate with respect to the total number of the manufactured rolled tobaccos, in order to take the smoke of the sampled rolled tobaccos in the tobacco-smoke analyzing apparatus and analyze their chemical substances. As the number of the manufactured rolled tobaccos increases, the number of the rolled tobaccos to be sampled also increases.

Rolled tobaccos such as cigarettes and cigars are held by holders in a plurality of smoke inlets formed in the tobacco-smoke analyzing apparatus (hereinafter referred to only as the "analyzing apparatus"). After the rolled tobaccos have been lit, air is sucked in the analyzing apparatus through the rolled tobaccos mounted in the smoke inlets at a predetermined pattern. In each holder is provided a Cambridge filter for collecting tar or the like. The smoke taken in the analyzing apparatus is analyzed by an analyzing unit so as to find the contents of other chemical substances in the smoke.

With the conventional analyzing apparatus, mounting of rolled tobaccos and holders, lighting and extinguishing of the rolled tobaccos and the removal of tobacco ashes or tobacco ends including cigarette butts or cigar ends have been performed manually. For a great number of rolled tobaccos to be analyzed, the same simple operation must be repeated for a long time. This adds inspecting burden to the inspector.

In order to overcome the problem, it has been demanded that the full operation of the analyzing apparatus be automated. Since, however, rolled tobaccos are likely to be broken easily, it has been difficult to automatically light the rolled tobaccos mounted in the smoke inlets and automatically extinguish the rolled tobaccos securely after they have burnt to a predetermined portion.

SUMMARY OF THE INVENTION

The object of this invention is to provide an apparatus for automatically taking in smoke of rolled tobaccos and analyzing the smoke, which automatically mounts rolled tobaccos in the smoke inlets, lights and extinguishes the rolled tobaccos, and removes tobacco ashes or tobacco ends without the help of the inspector.

The apparatus according to this invention has a smoke analyzing device which automatically takes in smoke of rolled tobaccos such as cigarettes and analyzes the chemical contents of the smoke. The smoke analyzing device is provided with a plurality of smoke inlets, in each of which a rolled tobacco is mounted.

In the vicinity of the smoke analyzing device mounting and demounting means for mounting and demounting rolled tobaccos in and from the smoke inlets are provided. The mounting and demounting means comprises a universal operating robot which mounts rolled tobaccos in the smoke inlets and removes tobacco ashes or tobacco ends from the smoke inlets with the operating hand.

There are provided end position detecting means for detecting tips of rolled tobaccos and extinguishing position detecting means for detecting the position at which the rolled tobaccos are to be extinguished. The operating hand is provided with lighting means for lighting the tips of the rolled tobaccos and cutting-off means for cutting off the rolled tobaccos at the portions at which they are to be extinguished.

Such an apparatus for automatically analyzing smoke of rolled tobaccos not only can mount and demount rolled tobaccos in and from the smoke inlets but also can detect the positions of the tips of the rolled tobaccos, move them to lighting means, ensure, cut off the rolled tobaccos at the portions to be extinguished and ensure the rolled tobaccos are extinguished. Therefore, the delicate operation which must have been relied on the operator with the conventional apparatus can be automated, and smoke analyzing of rolled tobaccos can be carried out fully automatically.

The preferred embodiment according to this invention is provided with means for automatically removing tobacco ashes and cut-off burnt portions of the rolled tobaccos and means for collecting and exhausting tobacco smoke such that the outer atmosphere of a room in which smoke analyzing is performed is retained clean and safety in the room is ensured as well.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENT

This invention will be explained by way of the preferred embodiment with reference to the accompanying drawings.

Figure 1:
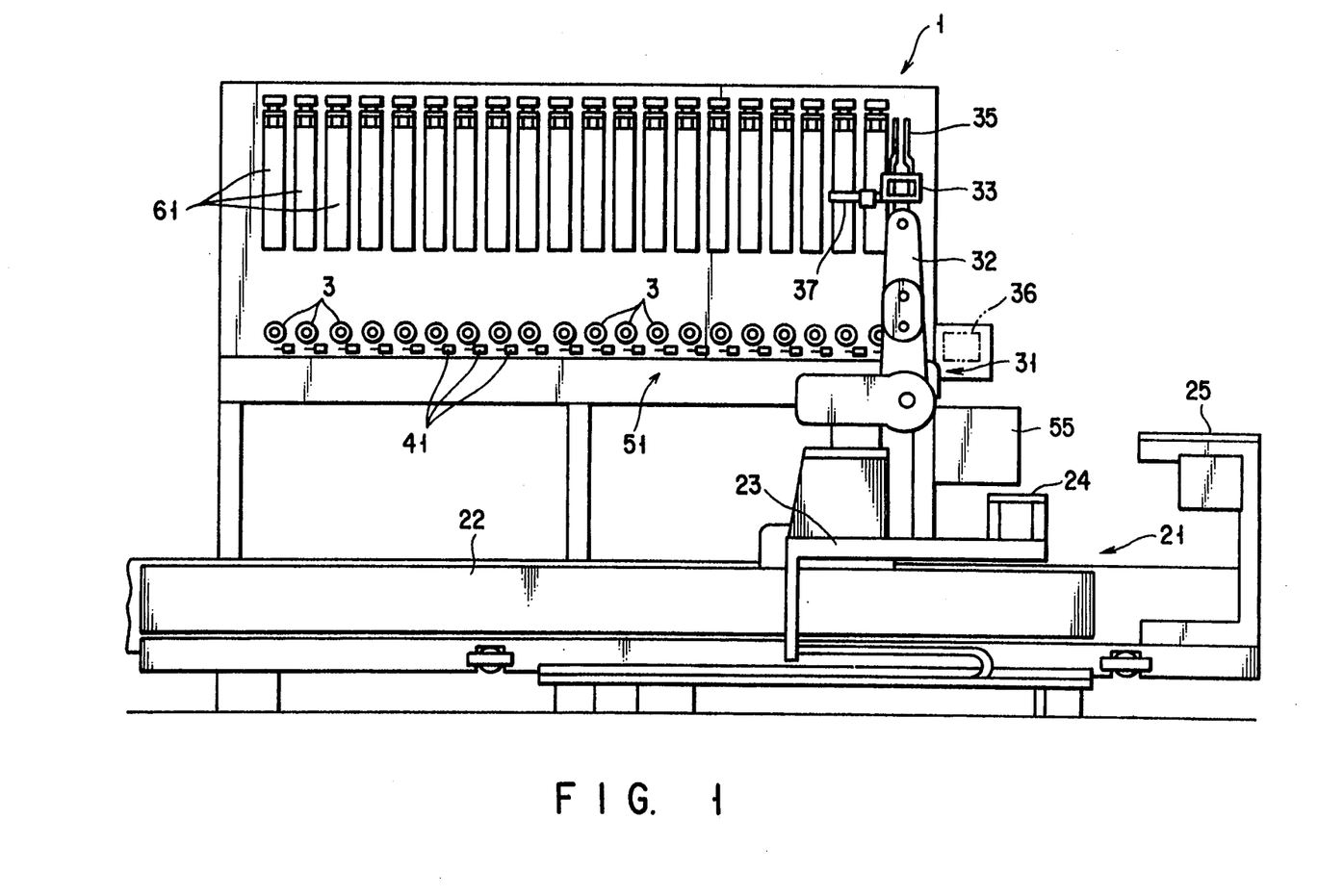
FIG. 1 is a front view of the overall automatic smoke analyzing device according to one embodiment of this invention.
Figure 2:
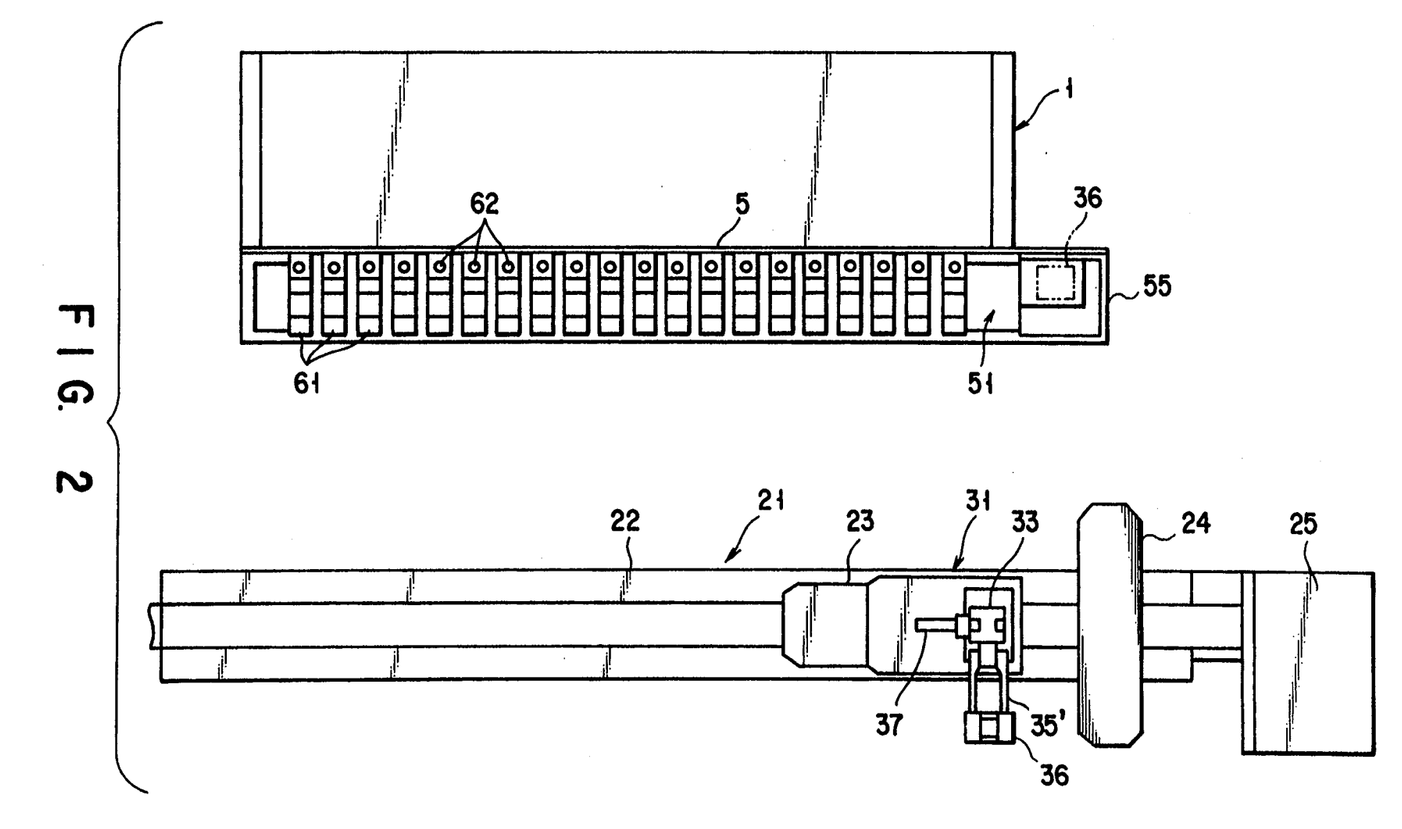
FIG. 2 is a plan view of the overall automatic smoke analyzing device of FIG. 1.
Figure 3:
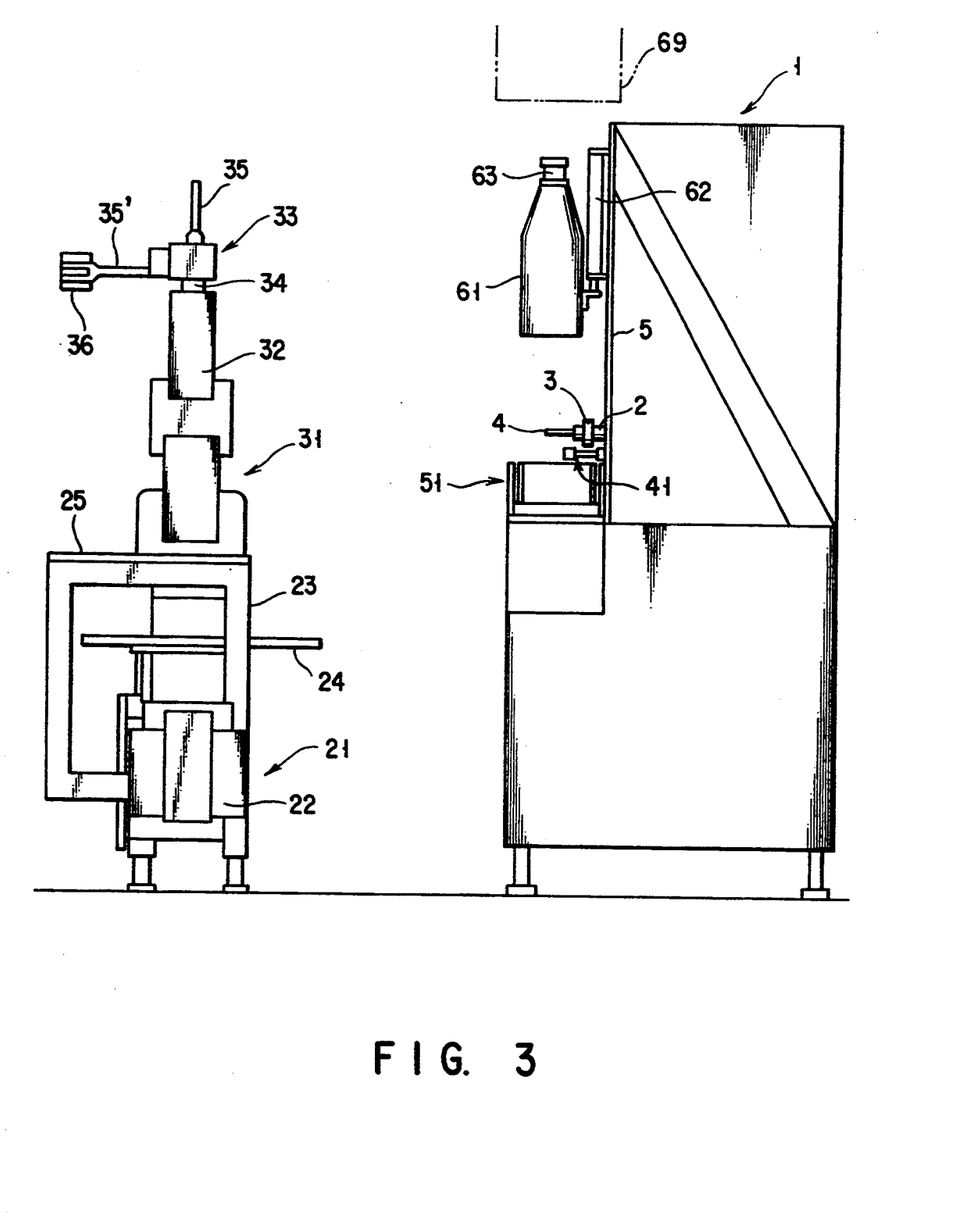
FIG. 3 is a side view of the overall automatic smoke analyzing device of FIG. 1.

FIGS. 1 to 3 show one embodiment of the overall automatic analyzing device according to this invention. FIG. 1, FIG. 2 and FIG. 3 show its front view, its plan view and its side view, respectively.

The main body 1 of the automatic analyzing apparatus has a front plate 5 from which a plurality of smoke inlets 2 project. A holder 3 is provided on each smoke inlet 2 and mounts a rolled tobacco 4 such as a cigarette or a cigar in the smoke inlet 2.

Figure 4:
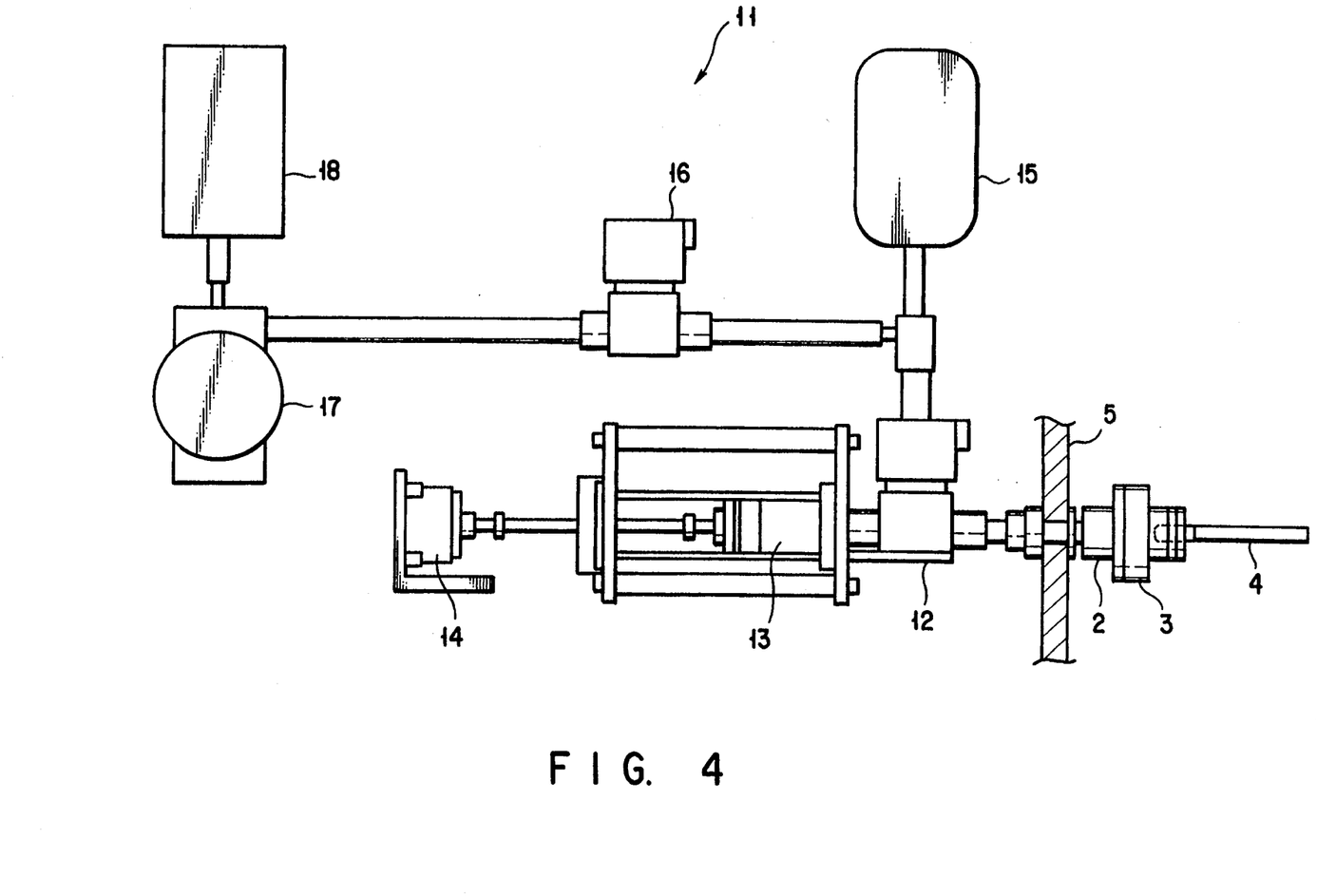
FIG. 4 is a side view of a smoking mechanism.

As shown in FIG. 4, a smoking mechanism 11 is aligned with each smoke inlet 2 in the main body 1. Each smoking mechanism 11 is provided with a cylinder mechanism 13 which communicates with the respective smoke inlet 2 and a respective smoke collecting bag 15 through a three-way valve 12. The cylinder mechanism 13 is moved back and forth by a driving mechanism 14 at a predetermined period so as to make change-over of the three-way valve 12 according to the movement of the cylinder mechanism 14. Air is intermittently sucked in through a rolled tobacco 4 mounted in the respective smoke inlet 2, and the gas sucked in is delivered to the smoke collecting bag 15 through the three-way valve 15.

The smoke collecting bag 15 is connected to a suction pump 17 through a two-way valve 16. The smoke delivered to the smoke collecting bag 15 is sucked by the suction pump 17. A gas analyzing unit 18 is connected to the exhaust port of the suction pump 17.

A Cambridge filter is housed in each holder 3. Tar in the smoke of the rolled tobacco 4 is collected by the Cambridge filter and the other chemical substances are analyzed by a gas analyzing unit 18.

In front of the main body 1, a moving mechanism 21 has a rail 22 disposed in parallel with the front plate of the main body 1. A moving table 23 is mounted on the rail 22 so as to be movable along it to an arbitrary position. On the moving table 23 are mounted a tobacco loading table 24 for loading rolled tobaccos to be tested and a holder loading table 25 for loading holders 3.

On the moving table 23, a robot 31 is provided of a commercially available universal arm type having an articulated arm 32 as a rolled tobacco mounting and demounting device. An operating hand 33 is fixed to the distal end of the arm 32 by a shaft 34 so as to be rotatable about the shaft 34. The shaft 34 is rotatable in the vertical direction with respect to the arm 32.

From the operating hand 33, a holding mechanism 35 extends for holding rolled tobaccos, another holding mechanism 35' disposed at the position of the holder 3 and at another position, for holding a cutting-off mechanism 36 for cutting off the burnt portion of the rolled tobaccos and a lighting mechanism 37 for lighting the rolled tobaccos. These mechanisms extend perpendicularly to each other. In operation, the operating hand 33 rotates around the shaft 34, and the shaft 34 rotates with respect to the arm 32 such that the mechanisms, which are to operate, face the front plate of the main body 1.

Upon mounting rolled tobaccos in the smoke inlets 2, the robot 31 is operated such that the holder 3 on the holder loading table 25 is held by the holding mechanism 35' and is mounted in the corresponding smoke inlet 2, and then the rolled tobacco is held by the holding mechanism 35 and mounted on the holder 3.

Next, the rolled tobacco mounted on the holder 3 is lit by the lighting mechanism 37. The smoke of the rolled tobacco is takes in the smoking mechanism 11 at a predetermined mode, and then the smoke is analyzed.

In the vicinity of each smoke inlet 2, an extinguishing position detecting mechanism 41 is provided which has an infrared ray sensor. The infrared ray sensor detects the infrared rays radiated from the burning portion of the rolled tobacco at which the rolled tobacco is to be extinguished.

Then, the robot 31 is operated such that the holding mechanism 35' of the operating hand 35 holds the cutting-off mechanism 36 which is located at the different position. The burnt portion of the rolled tobacco is cut off by the cut-off mechanism 36 and the rolled tobacco is extinguished. The smoking mechanism 11 continues its operation so as to suck in all smoke retained in the extinguished rolled tobacco.

After the cutting-off, the robot 31 is operated such that the holding mechanism 35 faces the front plate 5 of the main body 1 and then holds the tobacco ashes or tobacco end and pull it off. The process beginning with the mounting of rolled tobacco 4 and ending with the removal of tobacco ashes or a tobacco end is repeated five times, and then the holder 3 is removed from the smoke inlet 2 by the holding mechanism 35'.

The robot 31 is moved again by means of the moving mechanism 21 so as to be disposed in front of the next smoke inlet 2 and the same process as the above-mentioned is repeated. This process automatically continues until the process at the final smoke inlet 2 is completed.

There will be described a unit used in the automatic smoke analyzing device, for detecting the accurate position of the tip ends of the rolled tobaccos mounted in the smoke inlets 2 and for ensuring the lighting of the tips of the rolled tobaccos.

Figure 5:
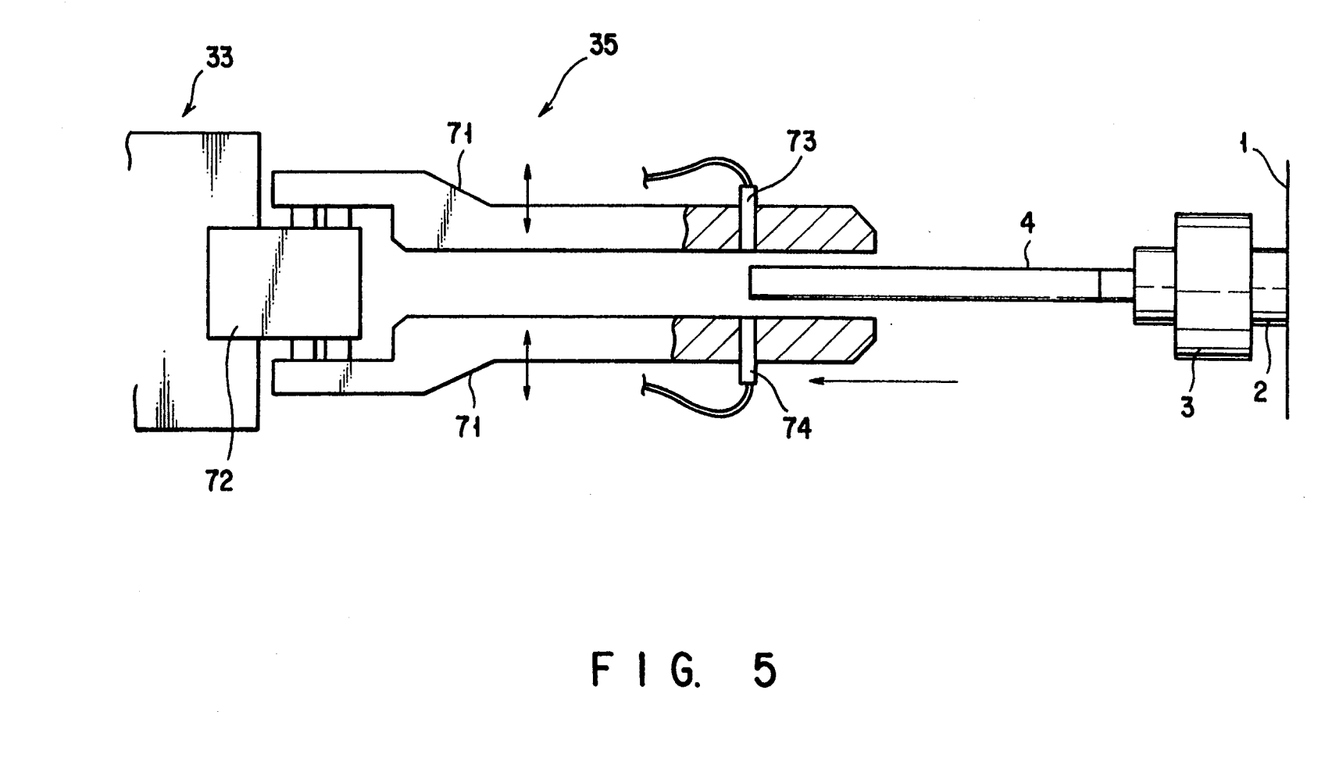
FIG. 5 is a plan view of a holding mechanism.

As shown in FIG. 5, the holding mechanism 35 of the operating hand 33 has a pair of fingers 71 closed and opened by means of a driving mechanism 72 with the fingers 71 maintained parallel to each other. When the fingers 71 are closed, they hold a rolled tobacco.

An optical detector comprises light source 73 such as an LED provided in the forward end portion of one of the fingers 71 and a photodiode 74 provided in the forward end portion of the other finger 71 opposed to the light source 71. Light emitted from the light source 73 is received by the photodiode 74. When an object, i.e., a rolled tobacco exits between the fingers 71, i.e., between the light source 73 and the photodiode 74, the light from the light source 73 is interrupted by the rolled tobacco.

After mounted a rolled tobacco 4 in the respective inlet 2 with the fingers 71 opened, the robot 31 is operated so as to place the rolled tobacco 4 between the fingers 71 and then moves the holding mechanism 35 in the axial direction of the rolled tobacco 4. When the light source 73 and the photodiode 74 face an intermediate portion of the rolled tobacco 4, the light from the light source 73 is interrupted by the rolled tobacco 4 and thus the photodiode 74 does not detect the light. As the holding mechanism 35 is further moved and the light source 73 and the photodiode 74 exceed the tip of the rolled tobacco 4, the light from the light source 73 is incident on the photodiode 74, whereby the tip of the rolled tobacco 4 is detected.

The robot 31 memorizes the position of the tip of the rolled tobacco 4 in this state. Then, the heater of the lighting mechanism 37 attached to the operating hand 33 is directed so as to face the front plate of the main body 1. The heater of the lighting mechanism 37 is moved to a position closed to the tip of the rolled tobacco 4 and lights the same. In this case, the movement of the lighting mechanism 37 is controlled according to the information on the position of the tip of the tobacco 4. The heater move to a position closed to the tip of the rolled tobacco 4 so as to light the same securely. The heater can be prevented from abutting against the tip of the rolled tobacco 4 so strongly that the rolled tobacco 4 is displaced from the heater.

The rolled tobacco 4 is burnt from its tip to a predetermined intermediate portion (i.e., the extinguishing position) separated from the tip position as a datum position by a predetermined length.

An extinguishing position detecting mechanism 41 can be set at the extinguishing position of the rolled tobacco. When the burning of the rolled tobacco 4 which has started at its tip arrives at the extinguishing position, the extinguishing position detecting mechanism 41 detects it, and the rolled tobacco 4 is cutoff at the extinguishing position by the cutting-off mechanism 36. Then, the rolled tobacco 4 stops burning.

Figure 6:
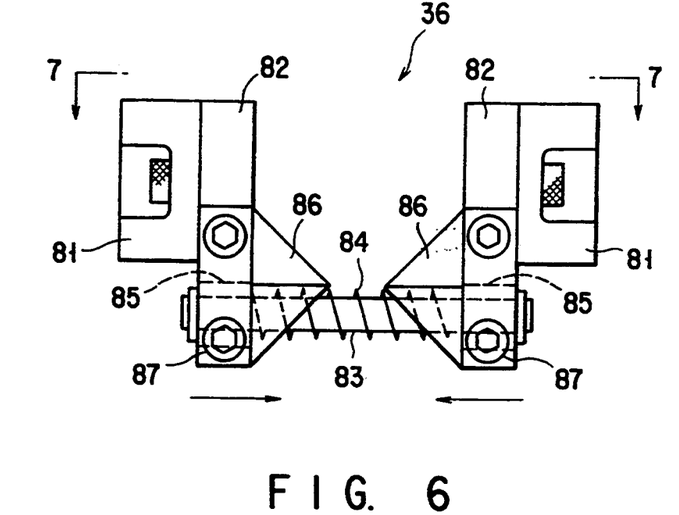
FIG. 6 is a front view of a cutting-off mechanism.
Figure 7:
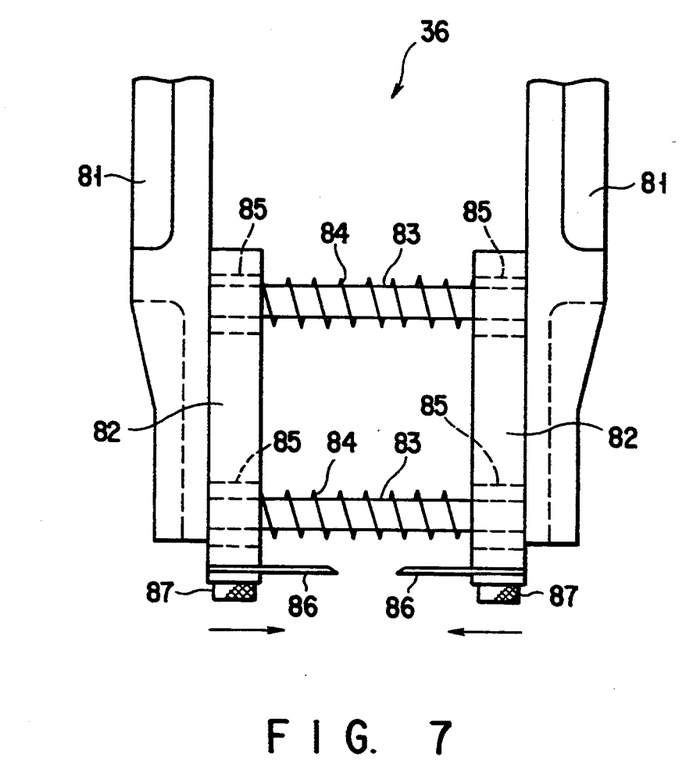
FIG. 7 is a view along line 7—7 in FIG. 6.

The cutting-off mechanism 36 will be described with reference to FIG. 6. The cutting-off mechanism 36 is provided with a pair of chucking members 81 which project from the operation hand 33 and are moved toward and away from each other by means of an opening and closing mechanism (not shown) provided on the operating hand 33. An opening and closing member 82 is removably connected to the front portion of each chucking member 81. The opening and closing members 82 are movable toward and away from each other together with the respective chucking members 81. Two slide bushes 85 are formed in the lower portion of each opening and closing member 82. Two guide rods 83 are slidably inserted in the slide bushes 85 of both opening and closing members 82 such that the guide rods 83 allow for the accurate movement of the opening and closing members 82. Between both opening and closing members 82, a compression coil spring 84 is disposed for urging the opening and closing members 82 to be separated from each other.

A pair of thin plate-like cutting blades 86 are connected by bolts 87 to the forward ends of the opening and closing members 82 so as to be opposed to and extend toward each other and to be replaced easily by removing the bolts 87. The forward portion of each cutting blade 86 has a triangular form such as an isosceles triangular shape whose apex is directed toward the other cutting blade 86 and whose both sides adjacent to the apex form cutting edges. The apexes of both cutting blades 86 are disposed opposed to each other. One of the cutting blades 86 is displaced by a thickness of each cutting blade from the other cutting blade 86 in the direction of its thickness. As the opening and closing members 82 approach each other, the forward portions of the triangular cutting blades 86 come to overlap each other.

With the opening and closing members 82 separated, the cutting-off mechanism 36 is moved to the position at which a rolled tobacco 4 to be cut is placed, and the rolled tobacco 4 is disposed between the two opening and closing members 82. Thereafter, the cutting-off mechanism 36 is moved in the axial direction of the rolled tobacco to the position at which the cutting blades 86 cut off the rolled tobacco 4, i.e., slightly behind the extinguishing position of the rolled tobacco 4.

Figure 8:
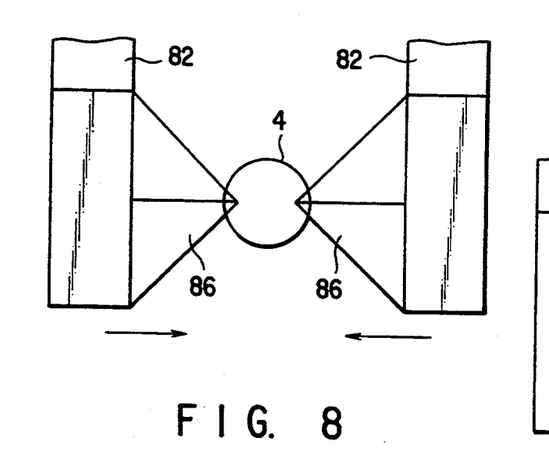
FIG. 8 is a general view illustrating the cutting-off operation of the cutting-off mechanism.
Figure 9:
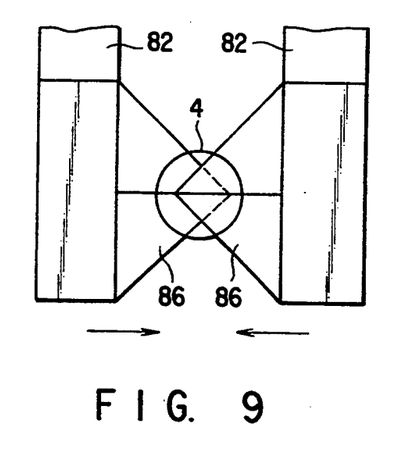
FIG. 9 is another general view illustrating the cutting-off operation of the cutting-off mechanism.

As the chucking members 81 are moved toward each other by the opening and closing mechanism, the opening and closing members 82 as well as the cutting blades 86 approach each other. As shown in FIG. 8, the apexes of the cutting blades 86 are stuck in the rolled tobacco 4 at two opposed lateral sides thereof. As the cutting blades 86 further approach each other, the cutting edges formed on the inclined sides of the triangular cutting blades 86 gradually cut the rolled tobacco 4. The cutting blades 36 advance further and overlap each other to cut off the rolled tobacco 4 completely, as shown in FIG. 9. After the burnt part of the rolled tobacco 4 has been cut off, the rolled tobacco is extinguished.

The smoking mechanism 11 is operated for a predetermined time after the cutting-off and extinction of the rolled tobacco 4 so as to take in smoke still remaining in the residual portion of the rolled tobacco 4 and analyze the taken-in smoke.

There will be described the extinguishing position detecting mechanism 41 which detects infrared rays radiated from the rolled tobacco when the rolled tobacco is burnt to the extinguishing position. Upon sensing the infrared rays from the rolled tobacco, the mechanism 41 moves the cutting-off mechanism 36.

Figure 10:
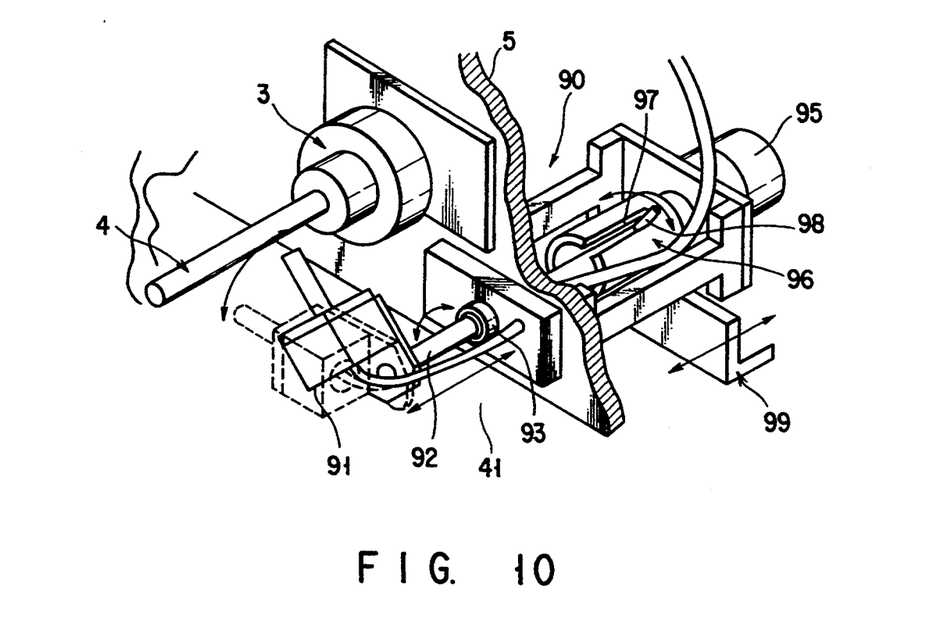
FIG. 10 is a perspective view of an extinguishing position detecting mechanism.

The extinguishing position detecting mechanism 41 has a detecting head 91 disposed slantwise below the smoke inlets 2 and connected to the forward end of a rod 92. The detecting head 91 can be reciprocated and rotated by a head moving mechanism 90. The rod 92 extends horizontally through the front plate 5 of the main body 1 and is rotatably and slidably supported by a bearing 93 provided on the front plate 5.

Within the main body 1, a rotary actuator 95 is connected to a cylindrical sleeve 96 formed with a pair of diametrically opposed and axially extending slits 97. Diametrically opposed pins 98 extend perpendicularly outward from the rear end portion of the rod 92. The rear end portion of the rod 92 is inserted in the sleeve 96 with the pins 98 engaged with the slits 97. Thus, the rod 92 and the detecting head 91 are rotated by the rotary actuator 95.

In the main body 1, a moving member 99 is engaged by one of the pins 98 of the rod 92 and reciprocated axially of rod 92 by means of an actuator (not shown). As the rod 92 reciprocates axially, the detecting head 91 also moves back and forth.

Figure 11:
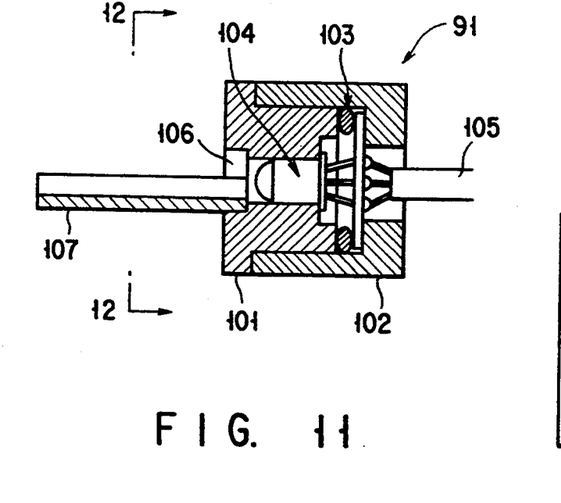
FIG. 11 is a longitudinal cross-sectional view of a detecting head.
Figure 12:
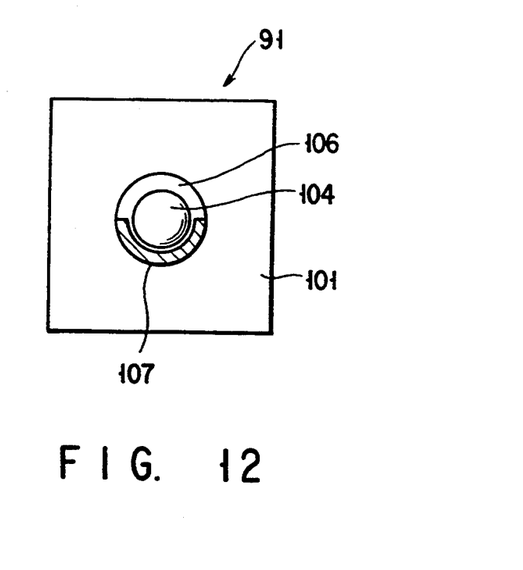
FIG. 12 is a cross sectional view along line 12—12 in FIG. 11.

As shown in FIGS. 11 and 12, the detecting head 91 has a housing 101 and 102 which are assembled together with an O-ring interposed therebetween. In the housings 101 and 102, an infrared ray sensor 104 is mounted. The sensor 104 comprises an infrared-ray detecting element such as a Ge photodiode having a high sensitivity for infrared rays of short wavelengths emitted from the extinguishing position of the rolled tobacco.

An opening 106 is formed in the housing 101 through which infrared rays enter the infrared ray sensor 104. A hood 107 having a semicircular cross section extends outward from the opening 106 and is arranged such that the arcuated surface of the hood 107 is directed forward, i.e., toward the tip of the rolled tobacco and the edges thereof are directed rearward, i.e., toward the rear end of the rolled tobacco.

The operation of the extinguishing position detecting mechanism 41 will be described.

First, the extinguishing position detecting mechanism 41 is retracted. The moving member 99 pushes out the rod 92 through the pin 98, thereby advancing the detecting head 91 by several centimeters. Then, the moving member 99 returns to the starting position so as to allow the detecting head 91 to move back and forth freely. The rod 92 is rotated such that the hood 107 of the detecting head 91 takes a horizontal posture. In this way, the detecting head 91 is prevented from interfering with the arm 32 of the robot 31, the holding mechanism 35, etc. upon mounting of the holder 3 and a rolled tobacco 4.

After a rolled tobacco 4 has been mounted and the tip of the rolled tobacco has been detected by the device for detecting the position of the tip of the rolled-tobacco (the end position detecting means), the extinguishing position of the rolled tobacco, i.e., the length between the tip of the rolled tobacco and the portion of the rolled tobacco to be extinguished is calculated, by making the position of the detected tip of the rolled tobacco as the datum position. The detecting head 91 advances and the rod 92 is rotated so as to direct the hood 107 of the detecting head 91 in the slantwise upper direction, i.e., toward a lateral side of the rolled tobacco. The hood 107 of the detecting head 91 is placed by the arm 32 of the robot 31 at the extinguishing position. Thereafter, the rolled tobacco is lit and burning starts.

The rolled tobacco 4 continues to be burnt and the burning portion arrives at a black line indicating the extinguishing position. Infrared rays having a relatively short wavelength radiated from the extinguishing position of the rolled tobacco 4 enter the infrared ray sensor 104. The infrared ray sensor 104 detects them and sends output signals to the robot 31. In response to the output signals, the rod 92 is rotated to make the hood 107 take a substantially horizontal position, whereby the hood 107 is prevented from interfering with the arm 32 of the robot 31 and the cutting-off mechanism 36 of the operating hand 33. In response to the output signals, the robot 31 is further operated to make the cutting-off mechanism 36 cut off the rolled tobacco 4 at its extinguishing position, thereby extinguishing the rolled tobacco 4.

The hood 107 of the detecting head 91 has a semicircular cross section. This improves the detecting accuracy of the extinguishing position of the rolled tobacco 4, as explained below.

Figure 13:
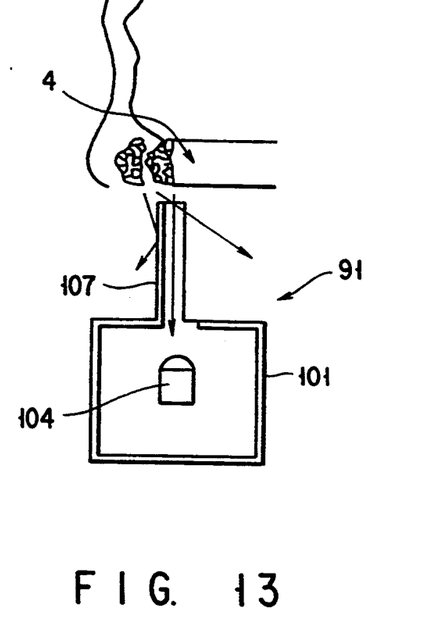
FIG. 13 is a general view illustrating the operation of the detecting head.

As shown in FIG. 13, infrared rays are radiated from all the extinguishing positions of the rolled tobacco in all directions. Out of the infrared rays coming from all the burning portions, the hood 107 allows only the ones radiated from the portion of the rolled tobacco 4 on and in the vicinity of the black line (the extinguishing position) to enter the infrared ray sensor 104 but prevents the infrared rays radiated from the portions away from its black line (i.e., the extinguishing position) from entering the infrared ray sensor 107.

Figure 14:
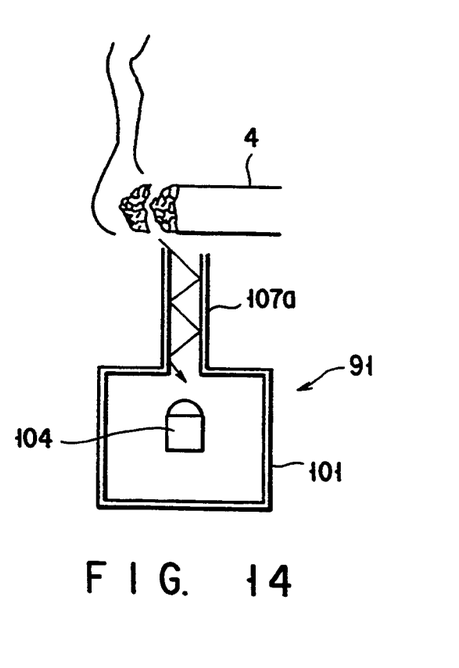
FIG. 14 is a general view illustrating the operation of the detecting head provided with a hood having a circular cross section.

If the hood 107a has a circular cross section as shown in FIG. 14, oblique rays from a portion of the rolled tobacco 4 which are close to its extinguishing position between the tip of the rolled tobacco 4 and its extinguishing position arrive at the forward end of the hood 107a. Such rays which entered the interior of the forward end of the hood 107a are repeatedly reflected on the inner surface of the hood 107a and reach the infrared ray sensor 104. However, such internal reflection does not occur on the hood 107 having a semicircular cross section. The smoking mechanism 11 continues to operate for a predetermined time after the rolled tobacco 4 has been cut off at the extinguishing position, and the smoke remaining in the unburnt portion of the rolled tobacco 4 is sucked in the smoking mechanism 11. Then, the smoke is analyzed and the analyzing result is improved.

Figure 15:
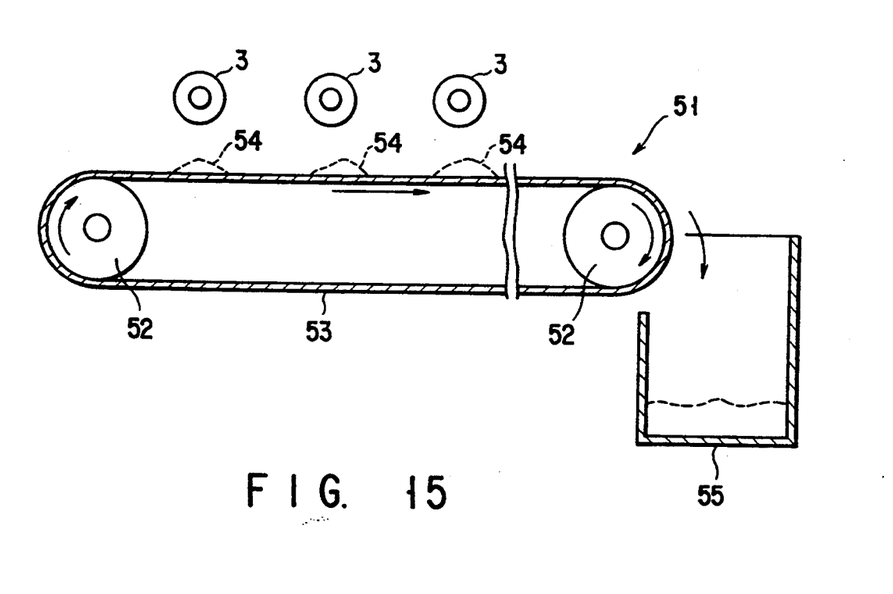
FIG. 15 is a longitudinal cross sectional view of a conveyor mechanism.

The automatic analyzing apparatus according to this invention is provided with a treating unit for exhausting tobacco ashes and tobacco ends, which will be described with reference to FIGS. 15 and 16.

The smoke inlets 2 are arranged horizontally in the front plate of the main body 1. Under the smoke inlets 2, a horizontal conveyer mechanism 51 is provided which has, on its both ends, a pair of rollers 52 around which a belt 53 is wound. The rollers 52 are rotated by a driving mechanism (not shown) to drive the belt 53 horizontally, as shown by the arrow in FIG. 5.

Figure 16:
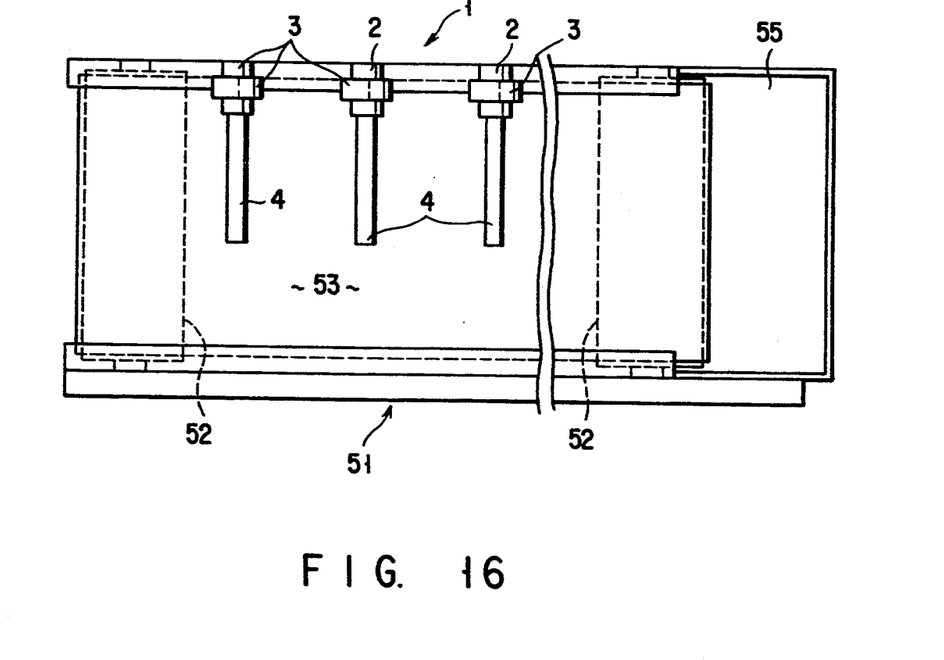
FIG. 16 is a plan view of the conveyer mechanism.

The belt 53 is made of heat-resistive material such a thin metal plate (stainless steel, for example) and has a width sufficiently larger than the length of rolled tobaccos as shown in FIG. 16. The belt 53 may be made of heat-resistive synthetic resin instead of metal.

An ash container 55 is disposed under the distal end portion of the conveyer mechanism 51. Tobacco ashes 54 and/or tobacco ends dropped on the belt 53 of the conveyer mechanism 51 are transported horizontally by the running belt 53 and fall into the ash container 55.

It is preferred that the conveyer mechanism 52 is operated only after ashes of the cut-off burnt portions of the rolled tobaccos have been removed from the smoke inlets 2 and dropped on the belt 53, such that the dropped burnt portions and/or tobacco ashes are immediately transported to the ash container 55 for their disposal.

Since the dropped tobacco ashes and tobacco ends are immediately transported to the ash container 55 by the conveyer mechanism 51, the smoke rising from the tobacco ashes and the tobacco ends does not enter other rolled tobaccos. This prevents adverse effects on the analyzing results and facilitates an accurate chemical analysis.

In this embodiment, the belt 53 is made of metallic material such as stainless steel. Since, therefore, the belt 53 has a high heat conductivity, heat produced from the dropped tobacco ashes, etc. is dissipated easily and is ensured to be extinguished in a short time.

Figure 17:
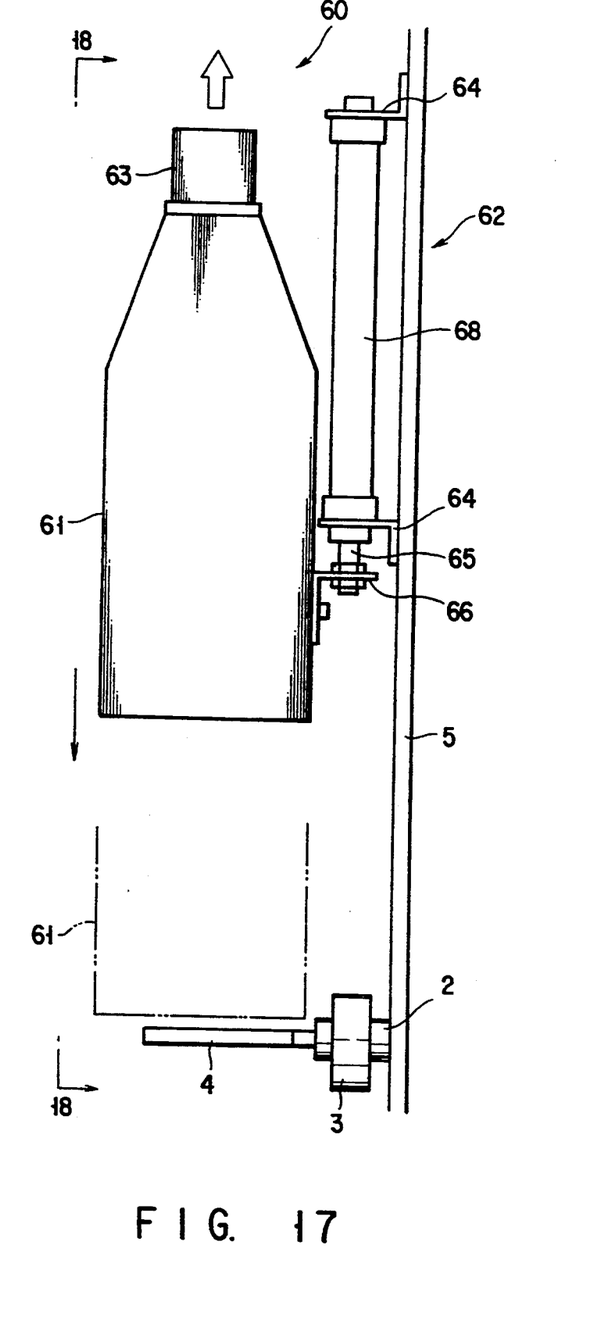
FIG. 17 is a side view of a smoke exhausting mechanism.
Figure 18:
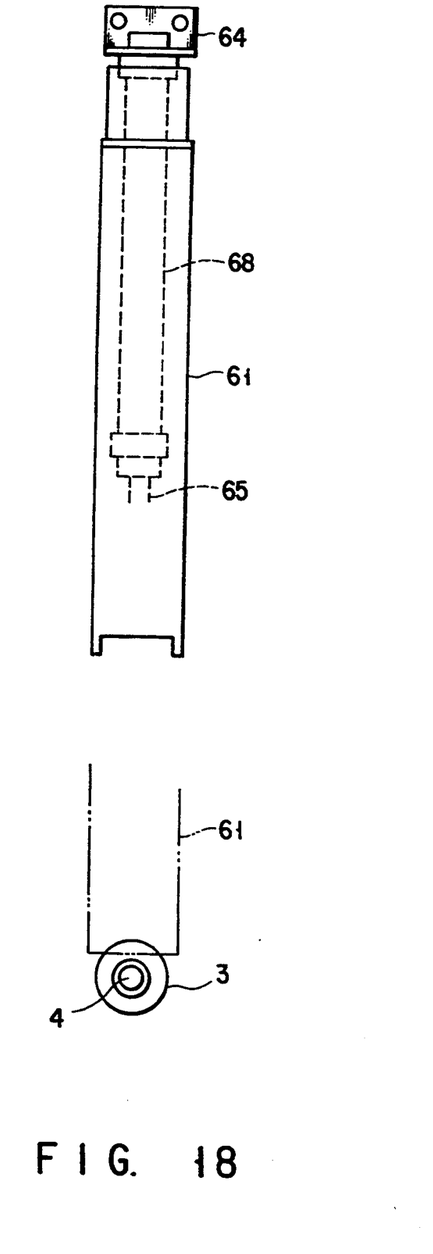
FIG. 18 is a cross sectional view along line 18—18 in FIG. 17.

As shown in FIG. 17 and 18, a smoke exhausting mechanism 60 is provided above the smoke inlets 2. The mechanism 60 is provided with a generally cylindrical smoke exhausting hood 61. The hood 61 has an opening at its lower end and is provided on its upper end with a small fan 63. Auxiliary smoke collected by the smoke exhausting hood 61 is sent upward by the fan 63 to the outer atmosphere of the test room through a smoke exhausting duct 69 (show in FIG. 3) provided in the vicinity of the ceiling of the test room.

The smoke exhausting hood 61 is moved upward and downward by means of a hood lifting mechanism 62 comprising an air cylinder unit 68 which is fixed substantially vertically by means of a fixture 64 to the front plate 5 of the main body 1 of the smoke analyzing device. The piston rod 65 extending downward from the lower end of the air cylinder unit has the lower end fixed to the smoke exhausting hood 61 by a fixture 66.

The hood 61 moves together with fan 63 when the holders 3 and rolled tobaccos 4 are mounted in the smoke inlets 2, the rolled tobaccos 4 are lit and cut off, and the tobacco ashes and/or tobacco ends are removed. Thus, the smoke exhausting hood 61 does not interfere with the arm 32 of the robot 31 and the operating hand 33.

While the smoke of the rolled tobaccos 4 is being sucked in the automatic smoke analyzing device, the smoke exhausting hood 61 is lowered by the hood lifting mechanism 62 to the vicinity of the rolled tobaccos 4 held in the smoke inlets 2 as shown by the two-dot chain lines in FIGS. 17 and 18. In consequence, the air flow around the smoke inlets 4 is controlled to take a predetermined stable state and smoke analysis is performed in a predetermined controlled state.

Since the fan 63 guides auxiliary smoke collected by the smoke exhausting hood 61 upward to the smoke exhausting duct, it is unnecessary to use a flexible smoke exhausting hose for connecting the smoke exhausting hood 61 to the smoke exhausting duct in this invention. This simplifies the structure of the apparatus and facilitates its maintenance.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An apparatus for automatically taking in smoke of rolled tobaccos and automatically analyzing the smoke, comprising:

a main body having a plurality of smoke inlets having rolled tobaccos mounted therein, for taking in smoke generated by said rolled tobaccos and analyzing chemical contents of said smoke;

mounting and demounting means, each provided at a respective one of said smoke inlets, for mounting one of said rolled tobaccos in said one of said smoke inlets and demounting said one of said rolled tobaccos from said one of said smoke inlets;

end position detecting means for detecting tip positions of said rolled tobaccos mounted in said smoke inlets;

extinguishing position detecting means for detecting extinguishing positions of said rolled tobaccos which are burning in said smoke inlets;

lighting means for lighting tips of said rolled tobaccos mounted in said smoke inlets;

cutting-off means for cutting off burnt portions from said rolled tobaccos at said extinguishing positions and extinguishing said rolled tobaccos; and wherein said lighting means moves to said tips of said rolled tobaccos which have been detected by said end position detecting means so as to light said tips of said rolled tobaccos, said extinguishing position detecting means detect said extinguishing positions, and said cutting-off means cuts off said burnt portions.

2. The apparatus according to claim 1, wherein said mounting and demounting means comprises a universal operating robot having an operating hand carrying said end position detecting means, said lighting means and said cutting-off means.

3. The apparatus according to claim 2, wherein said end position detecting means has optical detecting means mounted on said operating hand of said operating robot and moved axially of said rolled tobaccos mounted in said smoke inlets as said operating hand is moved, for detecting said tips of said rolled tobaccos.

4. The apparatus according to claim 3, wherein said operating hand of said operating robot has a pair of openable fingers for holding said rolled tobaccos and is operated so as to dispose said rolled tobacco between said fingers, and said optical detecting means comprises a light source provided in one of said fingers and an optical detecting element provided in the other finger, for detecting light from said light source, said optical detecting means being arranged such that said light from said light source is interrupted by said rolled tobacco when said rolled tobacco is disposed between said fingers and said optical detecting element detects said light from said light source to sense said tip of said rolled tobacco when said tip of said rolled tobacco passes beyond said light detecting element by as said operating hand moves along said rolled tobacco.

5. The apparatus according to claim 1, wherein said extinguishing position detecting means includes a detecting head provided at a position in a vicinity of each of said smoke inlets and movable between said position and a predetermined axial position of a respective rolled tobacco, each said detecting head comprising an infrared ray sensor, and said extinguishing position detecting means further includes a hood associated with each said detecting head projecting toward a predetermined position of a lateral side of a respective rolled tobacco, the hood blocking infrared rays emitted from positions other than extinguishing positions of said rolled tobacco and in a vicinity thereof such that the infrared rays blocked by the hood are prevented from entering said detecting head.

6. The apparatus according to claim 5, wherein said hood has a substantially semicircular cross section with a semicircular surface thereof facing said tip of said rolled tobacco.

7. The apparatus according to claim 2, wherein said cutting-off means has a pair of opening and closing members provided on said operating hand of said operating robot, each of said opening and closing members including a cutting blade having a triangular forward portion which extends toward the other opening and closing member and is defined by an apex and two side edges on both sides of said apex, said apex of said one of said opening and closing members being arranged opposed to said apex of said other opening and closing member, said triangular forward portions of said opening and closing members being arranged to overlap with each other, as said opening and closing members approach each other.

8. The apparatus according to claim 1, wherein ash exhausting means is provided under said smoke inlets and comprises a conveyer mechanism having a horizontally running heat-resistive belt and an ash container provided under a distal end portion of said conveyer mechanism, for receiving tobacco ashes and tobacco ends transported by said conveyer mechanism.

9. The apparatus according to claim 8, wherein said belt is made of a thin metal plate.

10. The apparatus according to claim 1, wherein smoke exhausting means is provided in a vicinity of said main body and comprises a smoke exhausting hood provided above said smoke inlets, for collecting auxiliary smoke rising from said rolled tobaccos mounted in said smoke inlets and burning, a fan for moving said auxiliary smoke collected in said smoke exhausting hood upward, and a hood lifting mechanism for moving said smoke exhausting hood vertically.

* * * * *